United States Patent [19]

Taylor

[11] Patent Number: 5,249,582

[45] Date of Patent: Oct. 5, 1993

[54] ORIENTED BIOPSY NEEDLE ASSEMBLY

[75] Inventor: Alan N. Taylor, Rockford, Mich.

[73] Assignee: Hart Enterprises, Wyoming, Mich.

[21] Appl. No.: 753,180

[22] Filed: Aug. 30, 1991

[51] Int. Cl.$^5$ ............................................. A61B 10/00
[52] U.S. Cl. ................................................... 128/754
[58] Field of Search ................ 128/749, 751, 753, 754; 606/167, 170, 171

[56] References Cited

U.S. PATENT DOCUMENTS

| | | | |
|---|---|---|---|
| D. 306,070 | 2/1990 | Akerfeldt | D24/25 |
| D. 309,014 | 7/1990 | Akerfeldt | D24/25 |
| 3,477,423 | 11/1969 | Griffith . | |
| 4,356,828 | 11/1982 | Jamshidi | 128/754 |
| 4,469,109 | 9/1984 | Mehl | 128/754 |
| 4,600,014 | 7/1986 | Beraha | 128/754 |
| 4,699,154 | 10/1987 | Lindgren | 128/754 |
| 4,735,215 | 4/1988 | Goto et al. | 128/754 |
| 4,881,551 | 11/1989 | Taylor | 128/754 |
| 5,121,751 | 6/1992 | Panalletta | 128/754 |

*Primary Examiner*—Max Hindenburg
*Attorney, Agent, or Firm*—Waters & Morse

[57] ABSTRACT

The oriented biopsy needle assembly includes a cannula hub assembly having a cannula hub fixedly attached to the proximal end of a cannula and a leg extending proximally from the proximal end of the cannula hub.. The cannula hub has a longitudinal coaxial bore therethrough axially aligned with and extending to the cannula. A stylet hub assembly fixedly attached to a sampling stylet includes a stylet hub at a proximal end, a shoulder portion, and a stem portion extending distally from the shoulder portion and terminating at a distal tip member. The distal tip member is slidably received on a rail of the leg extending proximally from the cannula hub to avoid undesirable rotational movement of the stylet and allow longitudinal movement of the stylet hub assembly on the rail only when the distal tip member is oriented such that the sharpened distal ends of the cannula and sampling stylet are oppositely directed. The distal tip member further includes a pair of distal guide teeth and a pair of proximal brace projections which cooperate with a rail stop at the proximal end of the rail to orientate the stylet hub assembly in a proximally retracted removably latched spaced relationship to the cannula hub assembly. Dislodging the tip member from the rail stop allows proximal withdrawal of the sampling stylet from the cannula so that multiple biopsies may be obtained with one insertion of the cannula.

7 Claims, 2 Drawing Sheets

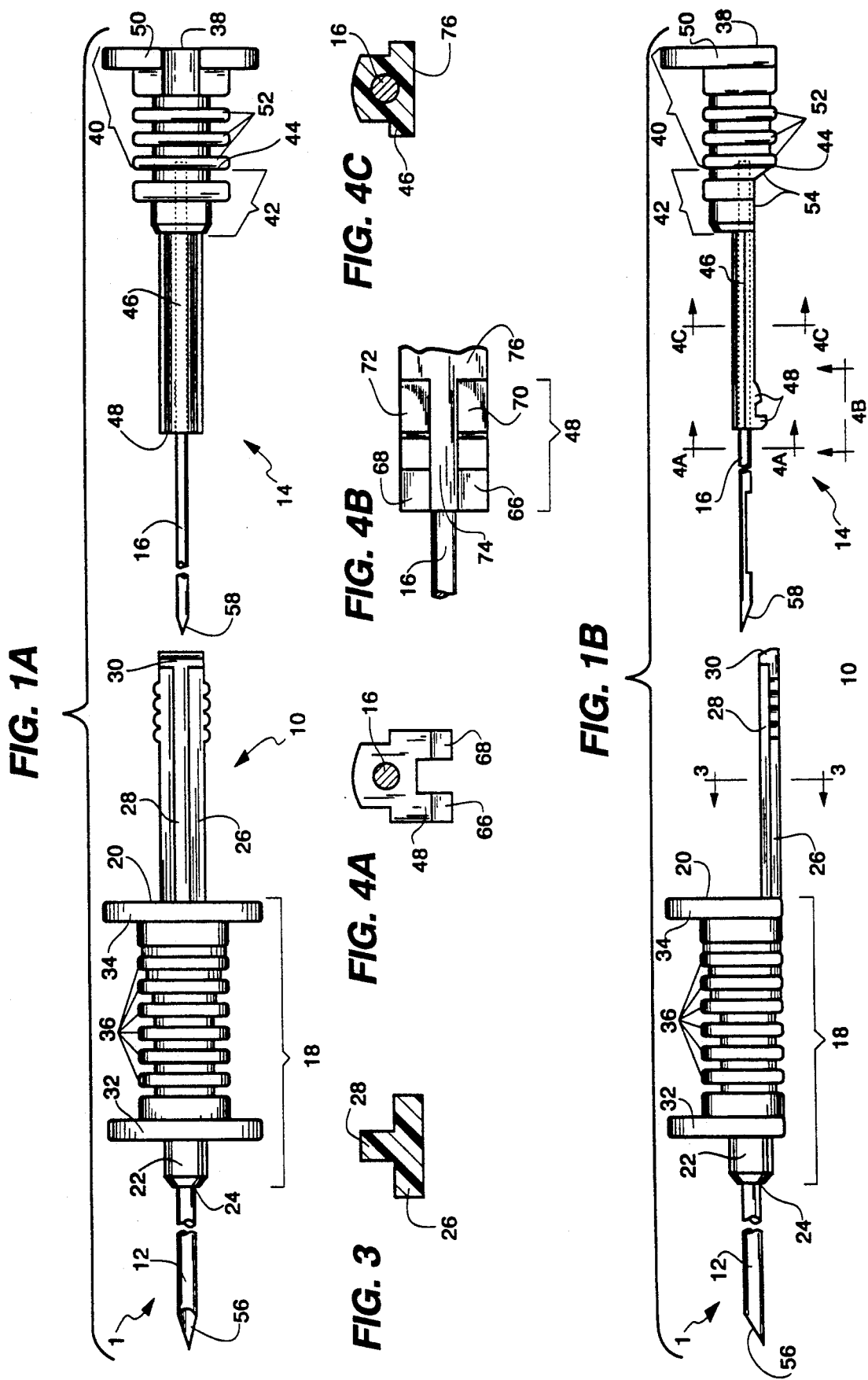

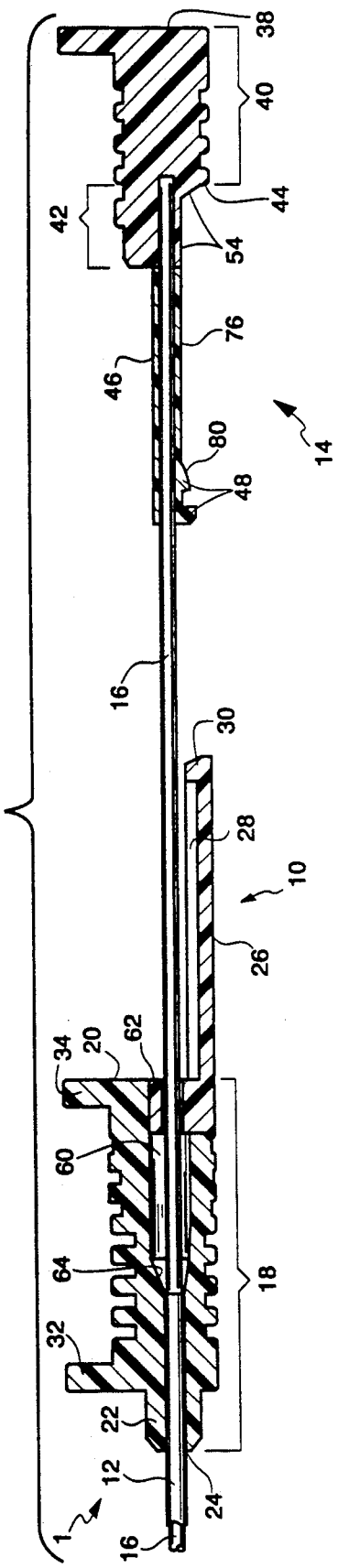
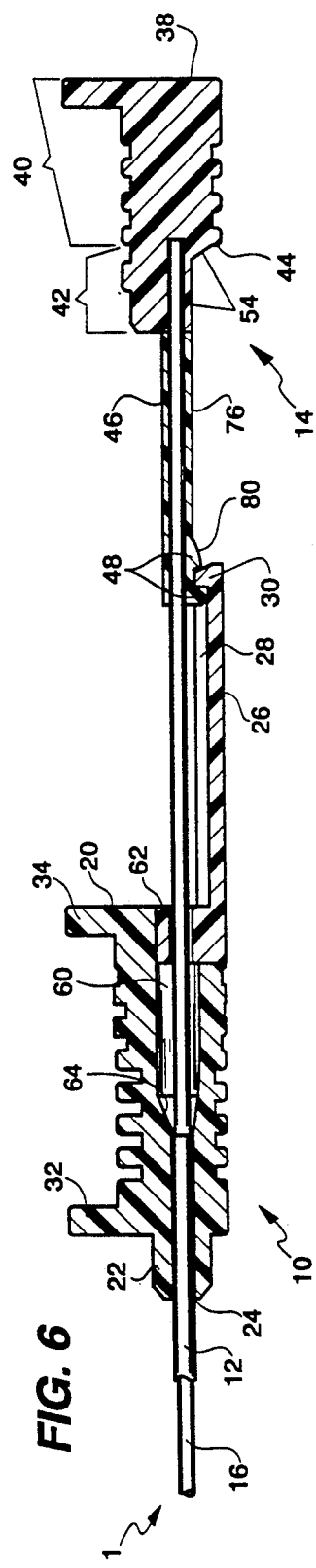
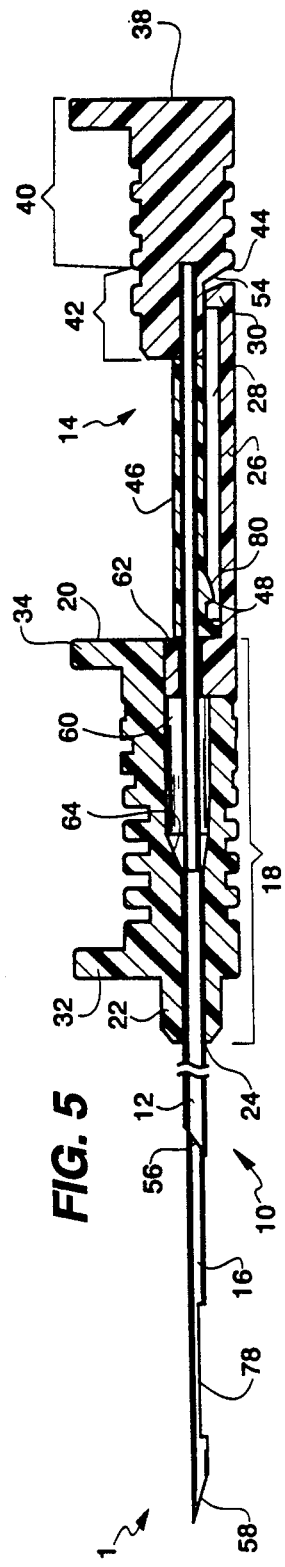

ORIENTED BIOPSY NEEDLE ASSEMBLY

BACKGROUND OF THE INVENTION

1. Field of the Invention

The present invention relates to a disposable soft tissue biopsy instrument or more specifically, a cannula and stylet assembly. The disposable biopsy instrument of the present invention provides an oriented, spaced relationship between a hub of an inner sampling stylet and a hub of an outer cannula. The assembly is oriented such that the sharpened distal ends of the cannula and of the sampling stylet are oppositely directed and cannula and stylet hub subassemblies of the needle assembly allow for quick proximal withdraw of the sampling stylet from the cannula for inspection of the sample without removal of the cannula from the biopsy site.

More specifically, the stylet and cannula hub subassemblies are constructed: (a) to provide for smooth forward advance of the stylet hub assembly onto a leg proximally extending from the proximal end of the cannula hub assembly with minimal force forwardly when an actuating device causes relative movement between the subassemblies; and (b) with a distal tip member of a stem portion of the stylet hub assembly and a rail stop at the proximal end of the rail of the leg of the cannula hub assembly which engage each other for positioning the cannula needle and stylet in a desired firing position, and which prevents accidental backout of the stylet hub assembly from the cannula hub assembly and undesirable rotation of the sampling stylet.

2. Description of the Related Art Including Information Disclosed Under 37 CFR §1.97-1.99

Sampling of inner tissue on humans and animals, a so-called biopsy, has become an increasingly common procedure for the diagnosis of malignancies and for other medical uses. Typically, biopsy instruments include a needle assembly comprising a hollow outer needle (cannula) and an inner needle (sampling stylet) slidably provided therewithin. The sampling stylet has a sharpened distal end and an adjacent biopsy sample-receiving notch which is telescopically disposed within the cannula and extendible from the distal end of the cannula. When so extended, the surrounding tissue expands into the sample-receiving notch of the sampling stylet. Thereafter the cannula is pushed forward to cover the stylet thus cutting-out a tissue sample which is thereby collected in the sample-receiving notch of the sampling stylet and retained by the surrounding outer cannula. When the tissue sample is taken, typically the entire needle assembly containing the collected tissue sample is withdrawn whereupon the sample can be taken out and analyzed.

The Travenol TRU-CUT ® biopsy needle available from Travenol Laboratories, Inc. of Deerfield, Ill. and the subject of U.S. Pat. No. 3,477,423 is an often used biopsy needle comprising a hollow tubular cutting cannula having a sharpened distal end attached to a plastic handle. A coaxial solid stylet telescopes within the cannula and is attached to a knob at its proximal end. The distal end of the stylet is sharpened and includes a traverse slot or specimen notch adjacent to the sharpened end. To obtain a biopsy sample using the Travenol needle, the physician positions the stylet up to or in front of the area to be biopsied, whereupon advancement of the needle assembly is halted. The stylet is then manually advanced distally of the cannula with the cannula held stationary. Upon advancement of the stylet, the specimen notch is exposed. Tissue surrounding the stylet contracts into the specimen notch and the cutting cannula is then manually advanced distally over the stylet, slowly shearing off the tissue entrapped in the stylet's specimen notch. The instrument is then withdrawn and the stylet advanced distally to expose the tissue for preparation for study. If the sampling was not successful, the stylet may be reinserted into the cannula, which remains positioned within the patient, and an attempt to reposition the assembly of the stylet and the cannula and repeat sampling can be made.

Such technique using this basic design of a biopsy instrument is referred to as a manual technique. One drawback to the manual technique is that it requires a great deal of manual dexterity and motor coordination, along with the use of both hands, to advance the stylet while maintaining the position of the cannula and then to maintain the position of the stylet while advancing the cannula.

The Beraha U.S. Pat. No. 4,600,014 discloses a transrectal prostate biopsy device which comprises a handle held in a physician's palm, and a guide tube extending forwardly of the handle. A cannula is slidably disposed within the guide tube and is movable from within the guide tube forwardly out of the distal end of the guide tube. A sampling stylet is telescopically disposed within the cannula and projects from the rear of the handle. A knob is provided at the proximal end of the stylet for extending a distal end of the stylet out of the distal end of the guide tube to expose a sampling thereon. The physician holds the handle in one hand using his index finger at the distal end of the guide tube to guide the instrument to a selected transrectal point on the prostate. Upon locating the point, one hand holds the instrument steady while the other hand pushes the stylet forward and then pushes the cannula over the stylet to sever the tissue within the sampling slot. The device is then withdrawn to gain access to the sample. In one embodiment of the device, the cannula, when in the retracted position, is spring loaded by means of a compressed spring. A release lever, which works against the compressed spring can be activated to release compression of the spring which then expands and pushes the cannula outwardly over the stylet.

A fully automatic instrument is described in U.S. Pat. No. 4,699,154. This instrument comprises a reusable, spring-loaded box-shaped housing or handpiece, which activates a disposable cannula and stylet set. Both the stylet and cannula are activated in rapid succession.

The instrument has the advantage of eliminating the dexterity and motor coordination necessary in use of manual devices and also eliminates the slow cutting action of the manually advanced cannula and replaces it with a very quick, clean cut.

The Goto et al U.S. Pat. No. 4,735,215 teaches a Soft Tissue Biopsy Instrument wherein a stylet extends through a cannula mounted in a distal outer barrel member and is press-fitted into a stylet hub that is press-fitted into a locking ring that is threadably received on a mounting ring fixed in a proximal outer barrel member. The stylet hub is received in an inner proximal barrel member. To remove the stylet the proximal outer barrel member must be unthreaded from the distal outer barrel member and then the locking ring/stylet hub must be unthreaded from the mounting ring.

In the Taylor U.S. Pat. No. 4,881,551 there is disclosed a soft tissue core biopsy instrument wherein a stylet extends through a proximal outer barrel member and distal inner barrel member, a proximal portion of which is received in the proximal outer barrel member and a cannula mounted to a cannula hub received in the distal inner barrel member. A proximal end of the stylet is mounted to a stylet hub which has a bifurcated proximal end portion defined by two fingers. Each finger has a detent thereon which is snap-fittingly received in a recess inside a proximal end of the proximal outer barrel member. The fingers are squeezed together to release the detents from the recess to remove the stylet. The mating recesses and detents serve to locate the stylet longitudinally and rotationally.

The oriented biopsy needle assembly of the present invention maintains the inner stylet hub and the outer cannula hub in a spaced oriented relationship whereby the user thereof may properly load or position the entire needle assembly into a reusable gun introduced without orientating the stylet hub and cannula hub into the gun individually. Alternatively, the orientation of the stylet and cannula hubs can be maintained such that the needle assembly can be positioned into the patient without necessarily, or first, loading the needle assembly into a reusable gun. This advantageously allows a physician to pre-position the needle assembly in a patient and scan the area to be biopsied confirming the correct position of the needle with scanner techniques such as MRI, CAT, and ultrasound independent of the reusable gun which is large and heavy and requires the user to maintain control of the gun handpiece at all times. Thereafter the stylet and cannula can be either advanced manually or with the aid of the automatic gun, such as the Radiplast AB tissue sampling device described in the Lindgren U.S. Pat. No. 4,699,154. The oriented spaced relationship between the cannula hub assembly and the stylet hub assembly conforms to the loading position of the Radiplast tissue sampling device merely by establishing a conforming length between the stylet hub and the cannula hub of the needle assembly of the present invention.

Further, the needle assembly of the present invention orients the assembly such that the sharpened distal ends of the stylet and cannula are oppositely directed and are so maintained free of undesirable rotation hindering successful biopsy collection.

Still further, the stylet is easily proximally removed from within the cannula such that examination of the biopsy sample may be taken without removing the cannula from the biopsy site.

The above attendant advantageous features also promote the desirable goals of minimizing the time required for biopsy and providing a disposable surgical instrument adapted for biopsy procedure utilizing scanning technologies.

SUMMARY OF THE INVENTION

According to the invention there is provided an oriented biopsy needle assembly comprising:
  a cannula hub assembly including a cannula hub having a proximal end and a distal end and a cannula extending distally from the cannula hub and having a sharpened distal end;
  a sampling stylet having a sharpened distal end and a biopsy sample receiving notch adjacent the distal end and being telescopically received within the cannula and extendible from the distal end of the cannula;
  the cannula hub having a longitudinal coaxial bore therethrough axially aligned with and extending to the cannula and further including a leg extending proximally from the proximal end of the cannula hub;
  a stylet hub assembly having a proximal end, a stylet hub at the proximal end, a shoulder portion at a distal end of the hub, and a stem portion extending distally from the shoulder portion and terminating at a distal tip member, the stylet hub, the shoulder portion, the stem portion, and the distal tip member being fixedly attached to the sampling stylet;
  first cooperating means on the stylet hub assembly and the cannula hub assembly for orienting the needle assembly so that the sharpened distal end of the cannula and of the sampling stylet are oppositely directed;
  second cooperating means on the stylet hub assembly and the cannula hub assembly for removably latching the stylet distal end with the cannula stem to orientate the stylet hub in a proximately retracted spaced relationship to the cannula hub when latched and to permit proximal withdrawal of the sampling stylet from the cannula so that multiple biopsies may be obtained with one insertion of the cannula when the cannula hub is unlatched from the stylet hub.

DESCRIPTION OF THE DRAWINGS

FIG. 1A is a longitudinal plan view of the oriented biopsy needle assembly of the present invention and shows a cannula hub assembly separate from a stylet hub assembly. FIG. 1B is a longitudinal side view of the assembly shown at FIG. 1A.

FIG. 2 is a longitudinal cross sectional view of the assembly similar to FIG. 1B but showing the stylet advanced within the cannula.

FIG. 3 is a cross sectional view through the cannula stem of the cannula hub assembly and is taken along line 3—3 of FIG. 1B.

FIG. 4A is a front plan view of the distal tip member of the distal stem of the stylet hub assembly, shows the stylet thereof in cross section, and is taken along line 4A—4A of FIG. 1B. FIG. 4B is a bottom plan view of the distal tip member of the distal stem of the stylet hub assembly and is taken along line 4B—4B of FIG. 1B. FIG. 4C is a cross sectional view through the distal stem of the stylet hub assembly and is taken along line 4C—4C of FIG. 1B.

FIG. 5 is a longitudinal cross sectional view through the assembly similar to FIG. 2 but shows the stylet stem and a recess surface of the shoulder portion of the stylet hub assembly fully received onto a rail of a leg extending proximally from the proximal end of the cannula hub.

FIG. 6 is a longitudinal cross sectional view through the assembly similar to FIG. 5 but shows the distal tip member of the stylet hub assembly stem proximally retracted and latched to a rail stop of the rail.

DESCRIPTION OF THE PREFERRED EMBODIMENTS

Referring now to the drawings, and more particularly to FIG. 1A, there is shown a longitudinal plan view of the oriented biopsy needle assembly 1 of the present invention in its two major components, namely a cannula hub assembly 10 including a cannula 12 and a stylet hub assembly 14 including a sampling stylet 16.

The cannula hub assembly 10 includes a cannula hub 18 having a proximal end 20 and a distal end 22 fixedly attached to the proximal end 24 of cannula 12, and a leg 26 extending proximally from and integral with the proximal end 20 of cannula hub 18. The leg 26 has a rail 28 integrally formed thereon extending lengthwise across the leg 26 and terminating into a rail stop 30. The cannula hub 18 has a longitudinal coaxial bore therethrough axially aligned with and extending to cannula 12.

The external surface of the cannula hub may comprise a number of diverse designs. For example, as illustrated at FIG. 1A and 1B, cannula hub 18 may include a traverse distal flange 32 and a traverse proximal flange 34 at the distal and proximal ends 22 and 20 respectively of cannula hub 18, and may further be ribbed therebetween with a plurality of cannula hub rib extensions 36.

Cooperating with the cannula hub assembly is a stylet hub assembly 14 having a proximal end 38, a stylet hub 40 at the proximal end, a shoulder portion 42 at a distal end 44 of the hub, and a stem portion 46 extending distally from shoulder portion 42 and terminating at a distal tip member 48. The stylet hub 40, shoulder portion 42, stem portion 46, and distal tip member 48 are fixedly attached to the sampling stylet 16 extending longitudinally therein and therefrom. The external surface of the stylet hub assembly 14 may, similar to the cannula hub 18, comprise a number of different designs. For example, as shown at FIG.1A and 1B, the proximal end 38 of the stylet hub assembly 14 may constitute a thrust handle 50, and the proximal portion 38 may be ribbed with a plurality of stylet hub rib extensions 52.

The shoulder portion 42 includes a recessed surface 54 generally coaxially aligned with rail stop 30 and leg 26. The distal tip member 48 of the stem portion 46 cooperates with the rail stop 30 of leg 26 to be removably latched thereto such as to orientate the stylet hub assembly 14 in a proximally retracted spaced relationship to the canula hub assembly 10. This spaced relationship may be defined to match the exact position necessary to properly load the oriented needle assembly 1 into a tissue sampling device of the type disclosed in U.S. Pat. No. 4,699,154 by merely establishing a corresponding length of the cannula hub assembly 10 to the stylet hub assembly 14 of the needle assembly 1 of the present invention. As shown in FIG. 1B, a longitudinal side view of the needle assembly illustrated at FIG. 1A, the distal tip member 48 is integral with stem portion 46 and cooperates with rail 28 of leg 26 for slidable longitudinal movement thereon only when the distal tip member is oriented upon the rail such that the cannula and sampling stylet sharpened distal ends 56 and 58 respectively are oppositely directed.

FIG. 2 is a longitudinal cross sectional view of the assembly similar to FIG. 1B but showing stylet 16 set within cannula 12. FIG. 2 also shows cannula hub longitudinal coaxial bore 60 fitted with a proximal guide spacer 62, and having a distal tapered inner wall 64. Longitudinal coaxial bore 60 is axially aligned with and extends through cannula hub 18 and funnels into cannula 12. The proximal guide spacer 62 serves to align sampling stylet 16 axially with cannula 12 and is generally coaxial with distal tip member 48 of stem portion 46 such as to be slidably received on the rail 28 of leg 26 to direct the sampling stylet 16 into the cannula 12.

The cooperative relationship of the leg 26 and stem portion 46 may be further understood by reference to FIG. 3 and FIG. 4 of the drawings. FIG. 3 is a cross sectional view through the leg 26 of the cannula hub assembly 18, taken along line 3—3 of FIG. 1B, and shows leg 26 having a rail 28 integrally formed thereon. FIG. 4A is a front plan view of the distal tip member 48 of the stem portion 46 taken along line 4A—4A of FIG. 1B and shows the sampling stylet 16 thereof in cross section. The distal tip member 48 includes integrally formed distal guide teeth 66 and 68 which, as shown at FIG. 4B, are spaced distally a short distance from proximal brace projections 70 and 72. FIG. 4B is a bottom plan view of the distal tip member 48 of the stem portion 46 of the stylet hub assembly 12 illustrating the spaced relationship between the distal guide teeth and the proximal brace projections and is taken along line 4B—4B of FIG. 1B. Slot 74 extends longitudinally between distal guide teeth 66 and 68 and adjacently aligned proximal brace projections 70 and 72, and is of a width to matedly engage and slidably receive the rail 28 of leg 26. The length between distal guide teeth 66 and 68 and proximal brace projections 70 and 72 corresponds to receive and removably latch rail stop 30 of the leg 26. FIG. 4C is a cross sectional view through the stem portion 46 of the style hub assembly 14 and is taken along line 4C—4C of FIG. 1B. Flat surface 76 of the stem portion 46, located proximally from distal tip member 48, allows the rail stop 30 to slide along the flat surface when the stem portion is advanced distally or retracted proximally.

As illustrated at FIG. 2, when the stylet 16 is inserted into cannula 12, the distal tip member 48 is generally coaxially aligned with longitudinal bore 60, the proximal guide spacer 62 of the cannula hub assembly 10, and the rail 28 of leg 26 of the cannula hub assembly 10. When the distal tip member 48 is set upon rail 28 of leg 26 of the cannula hub assembly 10 as in FIG. 5, the distal guide teeth and proximal brace projections prevent undesirable rotational movement of the stylet 16 while allowing longitudinal movement of the stylet hub assembly 14 on the rail with minimal force.

FIG. 5 is a longitudinal vertical cross section view through the needle assembly similar to FIG. 2 but shows the stem portion 46 and shoulder portion 42 of the stylet hub assembly 14 fully received onto the rail 28 of leg 26 extending proximally from the proximal end 20 of the cannula hub 18. In this position the rail stop 30 of leg 26 is received within the recess surface 54 of shoulder portion 42 of the stylet hub 40, and the distal tip member 48 of stem portion 46 abuts against guide spacer 62 fitted within longitudinal coaxial bore 60 of the cannula hub 18. FIG. 5 also illustrates the complete needle assembly 1 which includes cannula 12 extending distally from cannula hub 18 having a sharpened distal end 56, and a sampling stylet 16 having an oppositely directed sharpened distal end 58 and an adjacent biopsy sample receiving notch 78 ground therein. The stylet is telescopically received within the cannula and is extendable from the distal end of the cannula. It is preferable that the cannula and sampling stylet of the needle assembly have sharpened distal ends oppositely directed and that this relationship be maintained as such orientation is necessary for effective biopsy collection.

FIG. 6 is a longitudinal cross sectional view through the needle assembly similar to FIG. 5 but shows the stem portion 46 of the stylet hub assembly proximally retracted along rail 28 from the fully inserted position illustrated at FIG. 5. During proximal retraction of the stylet hub assembly 12, the distal guide teeth 66 and 68 and the proximal brace projections 70 and 72 of distal tip member 48 travel proximally along the rail 28 of leg 26 while the rail stop 30 of the leg 26 travels distally along flat surface 76 of the stem portion 46. When the proximal brace projections 70 and 72 contact the rail stop 30 during the proximal retraction movement, the rail stop leaves flat surface 76 of the stem portion 46 to travel upon the rear curved surface 80 of the proximal brace projections 70 and 72 respectively. When the course of travel of the rail stop 30 continues over the proximal brace projections, the rail stop engages distal guide teeth 66 and 68, which are greater in height than the proximal brace projections 70 and 72, such that the rail stop is releasably latched in the space between the guide teeth and brace projections. This releasable latching orientates the stylet hub assembly 14 in a proximately retracted spaced relationship to the cannula hub assembly 10. This spaced relationship may be defined to match the exact position necessary to properly load the oriented biopsy needle assembly 1 into a tissue sampling device of the type disclosed in U.S. Pat. No. 4,699,154 by merely establishing a corresponding length of the cannula hub assembly 10 to the stylet hub assembly 14. A user of the oriented biopsy needle assembly of the present invention may easily apply a dislodging force to the stylet hub assembly 14 to unlatched the distal tip member 48 from the rail stop 30 of leg 26 thereby permitting proximal withdrawal of the sampling stylet 16 from the cannula 12. Such proximal removal of the sampling stylet 16 allows examination of the biopsy collection to ensure adequacy of the sample size, or to determine that the sample is from the correct location, or to obtain multiple collections without removal of the cannula 12 from the biopsy site.

The present invention provides an oriented biopsy instrument which is disposable. The relatively simple two piece construction of a cannula hub assembly and a stylet hub assembly may be made at minimized cost of plastic resins suitable for injection molding. The cannula and stylet, of course, are made of stainless steel.

It is believed that the oriented biopsy needle assembly of the present invention in its described embodiment and with its attended advantages will be fully understood from the foregoing description, and that changes may be made in form, construction, and arrangement of the several parts thereof without departing from the spirit or scope of the invention or sacrificing any of the attended advantages. The preferred embodiments illustrated are not intended to be exhaustive or to limit the invention to the precise form disclosed. Accordingly, the scope of the invention is only to be limited as necessitated by the accompanying claims.

We claim:

1. An oriented biopsy needle assembly comprising:
   a cannula hub assembly including a cannula hub having a proximal end and a distal end and a cannula extending distally from said cannula hub and having a sharpened distal end, said cannula hub having a longitudinal coaxial bore therethrough axially aligned with and extending to said cannula and further including a leg extending proximally from the proximal end of said cannula, said leg of said cannula hub assembly having a rail thereon;
   a sampling stylet having a sharpened distal end and a biopsy sample receiving notch adjacent the distal end and being telescopically received within said cannula hub and cannula and extendible from said distal end of said cannula;
   a stylet hub assembly having a proximal end, a stylet hub at said proximal end, a shoulder portion at a distal end of said hub, and a stem portion extending distally from said shoulder portion and terminating at a distal tip member, said stylet hub, said shoulder portion, said stem portion, and said distal tip member being fixedly attached to said sampling stylet, said distal tip member of said stylet hub assembly having a slot extending longitudinally between a pair of distal guide teeth and a pair of proximal brace projections for mated slidable engagement with said rail when coaxially aligned thereto and only when said distal tip member is oriented so that said cannula and said sampling stylet sharpened distal ends are oppositely directed, said rail and said slot serving as a first means for angularly orienting said stylet and cannula, such that said sharpened distal ends of said cannula and of said sampling stylet are oppositely directed;
   second means on said stylet hub assembly and said cannula hub assembly for removably latching said stylet hub distal tip member with said leg such as to orientate said stylet hub in a proximately retracted spaced relationship to said cannula hub when latched and to permit proximal withdrawal of said sampling stylet from said cannula so that multiple biopsies may be obtained with one insertion of said cannula when said cannula hub is unlatched from said stylet hub.

2. The needle assembly of claim 1 wherein the second means for removably latching comprise a rail stop at the proximal end of said rail, said rail stop being releasably latched between said pair of distal guide teeth and said pair of proximal brace projections of said distal tip member of said stem portion when said brace projections are slidably retracted over said rail stop.

3. The needle assembly of claim 1 wherein said longitudinal coaxial bore is fitted with a guide spacer for directing said sampling stylet into the cannula.

4. The needle assembly of claim 1 wherein said external surface of the cannula hub is at least partially ribbed.

5. The needle assembly of claim 1 wherein said external surface of the stylet hub is at least partially ribbed.

6. The needle assembly of claim 1 wherein said external surface of said cannula hub includes a traverse flange near a distal end of said cannula hub and a traverse flange near said proximal end of said cannula hub.

7. The needle assembly of claim 1 wherein said proximal end of the stylet hub assembly includes of a thrust handle.

* * * * *